United States Patent [19]

Jensen et al.

[11] Patent Number: 4,933,353
[45] Date of Patent: Jun. 12, 1990

[54] LIPOPHILICALLY-SUBSTITUTED PIPERIDINE OXADIAZOLYL COMPOUNDS AND THEIR USE IN STIMULATING COGNITIVE FUNCTIONS (II)

[75] Inventors: Leif H. Jensen, Copenhagen; Per Sauerberg, Valby; Frank Wätjen, Vaerlose; Jens W. Kindtler, Kokkedal, all of Denmark

[73] Assignee: A/S Ferrosan, Sydmarken, Fed. Rep. of Germany

[21] Appl. No.: 236,550

[22] Filed: Aug. 25, 1988

Related U.S. Application Data

[63] Continuation of Ser. No. 89,747, Aug. 26, 1987, Pat. No. 4,837,241.

[30] Foreign Application Priority Data

Sep. 8, 1986 [DK] Denmark ............................. 4269/86
Dec. 12, 1986 [DK] Denmark ............................. 5971/86

[51] Int. Cl.$^5$ .................. C07D 413/04; A61K 31/44
[52] U.S. Cl. ...................................... 514/340; 546/277
[58] Field of Search ........................ 546/277; 514/340

[56] References Cited

FOREIGN PATENT DOCUMENTS

1542/87 9/1987 Denmark .

OTHER PUBLICATIONS

Iverson, L. L.: The Cholinergic Hypothesis of Dementia. Trends in Pharmacological Sciences, pp. 44–45, (1986).
Palacios, J. M. et al.: Mapping of Subtypes of Muscarinic Receptors in the Human Brain with Receptor Autoradiographic Techniques. Trends in Pharmacological Sciences, pp. 56–60, (1986).
Smith, C. J. et al.: Muscarinic Cholinergic Receptor Subtypes in Hippocampus in Human Cognitive Disorders, J. Neurochem., vol. 50 (3), pp. 847–855, (1988).
The Hydrophobic Fragmental Constant by Rekker, vol. 1 of Pharmaco Chemistry Library by Elsevier Scientific Publishing Company, (1977), pp. 78, 48, 119, 113–117.

Primary Examiner—Jane T. Fan
Attorney, Agent, or Firm—Gordon W. Hueschen

[57] ABSTRACT

New piperidine compounds having the formula

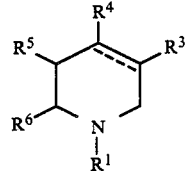

wherein
at least one of $R^3$, $R^4$, and $R^5$ are O-N  or  N-O
 \\ /        \\ /
  R'         R', and the other independently are H, $C_{1-6}$-alkyl,
wherein R' is H, $C_{1-8}$-alkyl, phenyl, thienyl, cyclopropyl, or $C_{1-3}$-alkoxymethyl; and
$R^1$ and $R^6$ independently are H or $C_{1-6}$-alkyl, and wherein $>$=$<$ is $>$CH—CH$<$ or $>$C=C$<$ ;

and salts thereof with pharmaceutically-acceptable acids.

The new compounds are useful in improving the cognitive functions of the forebrain and hippocampus of mammals, and are therefore useful in the treatment of Alzheimer's disease.

7 Claims, No Drawings

LIPOPHILICALLY-SUBSTITUTED PIPERIDINE OXADIAZOLYL COMPOUNDS AND THEIR USE IN STIMULATING COGNITIVE FUNCTIONS (II)

This is a continuation of application Ser. No. 089,747, filed Aug. 26, 1987, now U.S. Pat. No. 4,837,241 issued 6/6/89.

The present invention relates to therapeutically-active piperidine compounds, a method of preparing the same, and to pharmaceutical compositions comprising the compounds. The novel compounds are useful as stimulants of the cognitive function of the forebrain and hippocampus of mammals and especially in the treatment of Alzheimer's disease.

Due to the in general improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the muscarinic cholinergic neurons in *nucleus basalis*, which is part of *substantia innominata*. These neurons project to the prefrontal cortex and hippocampus and have a general stimulatory effect on the cognitive functions of the forebrain as well as of hippocampus, namely, learning, association, consolidation, and recognition.

It is a characteristic of Alzheimer's disease that although the cholinergic neurons degenerate, the postsynaptic muscarinic receptors in the forebrain and hippocampus still exist. Muscarinic cholinergic agonists are therefore useful in the treatment of Alzheimer's disease and in improving the cognitive functions of elderly people.

It is well known that arecoline (methyl 1-methyl-1,2,5,6-tetrahydropiperidine-3-carboxylate) is such a cholinergic agonist.

Arecoline, however, has a very short biological half life and a small separation between central and peripheral muscarinic effects. Furthermore, arecoline is a rather toxic compound.

Accordingly, it is an object of the invention to provide new muscarinic cholinergic compounds.

The novel compounds of the invention are piperidine compounds having the general formula I

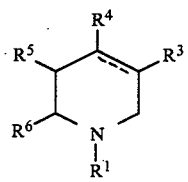

I wherein
at least one of $R^3$, $R^4$, and $R^5$ are

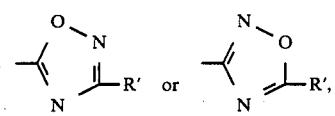

and the other independently are H, $C_{1-6}$-alkyl, wherein R' is H, $C_{1-8}$-alkyl, phenyl, thienyl, cyclopropyl, or $C_{1-3}$-alkoxymethyl; and
$R^1$ and $R^6$ independently are H or $C_{1-6}$-alkyl; and

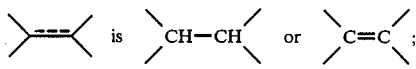

and salts thereof with a pharmaceutically-acceptable acids.

Examples of such salts include inorganic and organic acid addition salts such as hydrochloride, hydrobromide, sulphate, phosphate, acetate, fumarate, maleate, citrate, lactate, tartrate, oxalate, and similar pharmaceutically-acceptable inorganic or organic acid addition salts.

The invention also relates to a method of preparing the above-mentioned compounds. This method comprises (a) reacting a reactive derivative of a compound having the general formula II

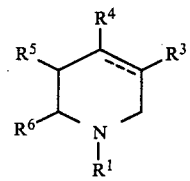

II wherein $R^1$, $R^6$, and

have the meanings defined above and
wherein one of $R^3$, $R^4$ and $R^5$ is $CO_2H$ or a reactive derivative thereof, such as an ester, and the others independently are H or $C_{1-6}$-alkyl, with a compound having the formula III $$R'-C(=NOH)NH_2 \quad \text{III}$$

wherein R' has the meaning defined above to form a compound of the general formula I, wherein one of $R^3$, $R^4$ and $R^5$ is

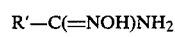

wherein R' has the meaning defined above,
(b) reacting a compound having the general formula II

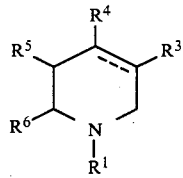

II wherein $R^1$, $R^6$, and

have the meanings defined above and wherein one of $R^3, R^4$, and $R^5$ is CN and the others independently are H or $C_{1-6}$-alkyl, with $NH_2OH$ to form a compound having the general formula II wherein one of $R^3$, $R^4$, and $R^5$ is $C(=NOH)NH_2$ and the other independently are H or $C_{1-6}$-alkyl, and reacting this compound with $R'$-COCl or $(R'$-$CO)_2O$ to form a compound of formula I, wherein one of $R^3$, $R^4$, and $R^5$ is

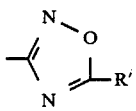

wherein $R'$ has the meaning defined above.

The pharmacological properties of the compounds of the invention can be illustrated by determining their capability to inhibit the specific binding of $^3$H-QNB ($^3$H-quinuclidinyl benzilate) by 50%. The inhibitory effect of a substance on $^3$H-QNB binding to brain membranes reflects the affinity of the substance for muscarinic acetylcholine receptors. (Yamamura, H. I. and Snyder, S. H., Proc.Natl.Acad.Sci. 71, 1725–29(1979). The test is carried out as follows:

Fresh whole forebrain from male Wistar rats (200–250 g) is homogenized by an Ultra-Turrax homogenizer (5–10 s) in volumes of 0.32 M sucrose. The homogenate is centrifuged at 4,300×g for 5 min. The pellet is discarded and the supernatant centrifuged at 40,000×g for 15 min. The final pellet is rehomogenized in 50 mM $KH_2PO_4$, pH 7.1 (1000 ml per g of original tissue) and this crude membrane preparation is used for binding assays. To 2.5 ml of tissue suspension is added 25 μl of test solution* and 25 μl $^3$H-QNB (1 nM final concentration). Samples are thoroughly mixed and incubated at 37° C. for 20 min. After incubation, samples are poured directly onto GF/C glass fiber filters under suction and immediately washed 2 times with 10 ml of buffer at 0° C. Non-specific binding is determined in duplicate using atropine (1 μg/ml, final concentration) as the test substance. The amounts of radioactivity on the filters are determined by conventional liquid scintillation counting. Specific binding is total binding minus non-specific binding.

\* Test compound is dissolved in 10 ml 96% ethanol (if necessary, acidified by 25 μl 1N HCl and heated on a steambath for less than 5 minutes) at a concentration of 0.22 mg/ml.

Three dilutions are made in 48% ethanol (1.1 μg/ml, 11 μg/ml and 11 μg/ml). Concentrations of 10, 100 and 1000 ng/ml (final concentration) are added to duplicate assays. 25–75% inhibition of specific binding must be obtained, before calculation of $IC_{50}$.

The test value will be given as $IC_{50}$ (the concentration/μg/ml) of the test substance which inhibits the specific binding of $^3$H-QNB by 50%).

$$IC_{50} = \text{(applied test substance concentration)} \times \frac{1}{\left(\frac{C_o}{C_x} - 1\right)} \, \mu g/ml$$

where $C_o$ is specific binding in control assays and $C_x$ is the specific binding in the test assay (the calculation assumes normal mass-action interaction).

Test results obtained by testing some compounds of the present invention will appear from the following Table 1.

TABLE 1

Structure: tetrahydropyridine with substituents $R^3$, $R^4$, $R^5$, $R^6$ on ring carbons and $R^1$ on nitrogen.

| $R^1$ | $R^3$ | $R^4$ | $R^5$ | $R^6$ | =< | Inhibition in vitro QNB binding (μg/ml) |
|---|---|---|---|---|---|---|
| $CH_3$ | 3-propyl-1,2,4-oxadiazol-5-yl | H | H | H | C=C | 3.5 |
| $CH_3$ | 3-cyclopropyl-1,2,4-oxadiazol-5-yl | H | H | H | C=C | 2.0 |
| $CH_3$ | 5-propyl-1,2,4-oxadiazol-3-yl | H | H | H | C=C | 3.2 |
| $CH_3$ | 3-tert-butyl-1,2,4-oxadiazol-5-yl | H | H | H | C=C | 4.9 |

TABLE 1-continued

[Piperidine structure with substituents R¹ (on N), R³, R⁴, R⁵, R⁶]

| R¹ | R³ | R⁴ | R⁵ | R⁶ | >C=C< | Inhibition in vitro QNB binding (μg/ml) |
|---|---|---|---|---|---|---|
| H | 3-cyclopropyl-1,2,4-oxadiazol-5-yl | H | H | H | >C=C< | 4.7 |
| CH₃ | 3-butyl-1,2,4-oxadiazol-5-yl | H | H | CH₃ | >C=C< | 3.3 |
| H | 3-ethyl-1,2,4-oxadiazol-5-yl | H | CH₃ | H | >C=C< | 7.5 |
| CH₃ | CO₂CH₃ | H | H | H | >C=C< | 21.0 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, penta-erythritol fatty acid esters, hydroxymethylcellulose, and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are conveniently unit dosages.

Tablets, dragees, or capsules having talc and/or a carbohydrate carrier or binder or the like, the carrier preferably being lactose and/or corn starch and/or potato starch, are particularly suitable for oral application. A syrup, elixir, or the like can be used in cases where a sweetened vehicle can be employed.

Generally, the compounds of this invention are dispensed in unit form comprising 1–100 mg in a pharmaceutically-acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| | |
|---|---|
| Active compound | 5.0 mg |
| Lactosum | 67.8 mg Ph. Eur. |
| Avicel TM | 31.4 mg |
| Amberlite TM IRP 88 | 1.0 mg |
| Magnesii stearas | 0.25 mg Ph. Eur. |

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease, as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity. Suitable dosage ranges are 1–100 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples, which are not to be construed as limiting:

EXAMPLE 1

1-Methyl-3-(3-methoxymethyl-1,2,4-oxadiazol-5-yl)-1,2,5,6-tetrahydropyridinium oxalate To a solution of sodium ethoxide (prepared from sodium (180 mg;7.8 mmol)), distilled ethanol (20 ml), molecular sieves (5 g), and methoxymethylcarboxamide oxime (832 mg; 8 mmol) were added. The mixture was stirred at room temperature for 10 min. whereafter arecoline, HBr (1.0 g; 4.23 mmol) was added. The mixture was heated at 80° C. for 12 hours, filtered, and evaporated in vacuo. To the residue was added water (10 ml) and the mixture was extracted with ether (3×25 ml). The combined extracts were dried (MgSO4) and evaporated in vacuo. Upon disolving the residue in ethanol (99.9%)(5 ml) a solution of oxalic acid (350 mg;3.9 mmol) in ethanol (99.9%)(10 ml) was added. Addition of ether gave an analytically pure product in a yield of 500 mg (40%). M.P. 153°–154° C.

EXAMPLE 2

1-Methyl-3-(3-methyl-1,2,4-oxadiazol-5-yl)-1,2,5,6-tetrahydropyridinium oxalate

This compound was synthesized as described above in Example 1 using acetamide oxime instead of methoxymethylcarboxamide oxime. Crystallization gave the title compound in 44% yield. M.P. 159°–160° C.

EXAMPLE 3

(RS)-1-Methyl-3-(3-methyl-1,2,4-oxadiazol-5-yl)-piperidinium oxalate

The compound was synthesized as described above in Example 2 using dihydroarecoline,HBr (Gloge et al., Br. J. Pharmac. Chemother. 27, 185 (1966)) instead of arecoline, HBr. Crystallization gave the title compound in 44% yield. M.P. 132°–133° C.

EXAMPLE 4

(RS)-1-Methyl-3-(3-ethyl-1,2,4-oxadiazol-5-yl)-piperidinium oxalate

The compound was synthesized as described above in Example 3 using propionamide oxime instead of acetamide oxime. Crystallization gave the analytically pure title compound in 33% yield. M.P. 145°–146° C.

EXAMPLE 5

(RS)-1-Methyl-3-(3-cyclopropyl-1,2,4-oxadiazol-5-yl)-piperidinium oxalate

The compound was synthesized as described above in Example 3 using cyclopropylcarboxamide oxime instead of acetamide oxime. Crystallization gave the title compound in 42% yield. M.P. 108°–109° C.

EXAMPLE 6

1-Methyl-4-(3-cyclopropyl-1,2,4-oxadiazol-5-yl)-piperidinium oxalate

The compound was synthesized as described above in Example 5 using 1-methyl-4-ethoxycarbonylpiperidinium chloride (Lambrecht and Mutschler, Arzneimittel Forsch.(Drug Res.) 23, 1427 (1973)) instead of dihydroarecoline. Crystallization gave the title compound in 50% yield. M.P. 168°–169° C.

EXAMPLE 7

1-Methyl-4-(3-methyl-1,2,4-oxadiazol-5-yl)-piperidinium oxalate

The compound was synthesized as described above in Example 6 using acetamide oxime instead of cyclopropylcarboxamide oxime. Crystallization gave the title compound in 53% yield. M.P. 173°–174° C.

EXAMPLE 8

1-Methyl-4-(3-propyl-1,2,4-oxadiazol-5-yl)-piperidinium oxalate

The compound was synthesized as described above in Example 6 using butanamide oxime. Crystallazation gave the title compound in 33% yield. M.P. 117°–118° C.

EXAMPLE 9

1-Methyl-3-(3-propyl-1,2,4-oxadiazol-5-yl)-1,2,5,6-tetrahydropyridinium oxalate

The compound was synthesized as described above in Example 1 using butanamide oxime instead of methoxymethylcarboxamide oxime. Crystallization gave the title compound in 32% yield. M.P. 153°–154° C.

EXAMPLE 10

1-Methyl-3-(3-ethyl-1,2,4-oxadiazol-5-yl)-1,2,5,6-tetrahydropyridinium oxalate

The compound was synthesized as described in Example 1 using propionamide oxime instead of methoxymethylcarboxamide oxime. Crystallization gave the title compound in 25% yield. M.P. 168°–169° C.

EXAMPLE 11

1-Methyl-3-(3-cyclopropyl-1,2,4-oxadiazol-5-yl)-1,2,5,6-tetrahydropyridinium oxalate The compound was synthesized as described above in Example 1 using cyclopropyl carboxamide oxime instead of methoxymethylcarboxamide oxime. Crystallization gave the title compound in 34% yield. M.P. 169°–172° C.

EXAMPLE 12

1-Methyl-3-(3-phenyl-1,2,4-oxadiazol-5-yl)-1,2,5,6-tetrahydropyridinium oxalate

The compound was synthesized as described above in Example 1 using benzamide oxime instead of methoxymethylcarboxamide oxime. Crystallization gave the title compound in 16% yield. M.P. 185°–186° C.

EXAMPLE 13 a: 1-Methyl-1,2,5,6-tetrahydropyridin-3-carboxamide oxime

To a solution of sodium methoxide, prepared from sodium (575 mg; 25 mmol) in methanol (30 ml), hydroxylammonium chloride (1,74 g; 25 mmol) was added. The mixture was stirred at room temperature for 30 min. and filtered. A solution of 1-methyl-3-cyano-1,2,5,6-tetrahydropyridine (Liberatore et al, Tetrahedron Letters. 46, 4735 (1968)) (1.65 g; 13.5 mmol) in methanol (20 ml) was added to the filtrate. The reaction was stirred at room temperature for 20 hours and evaporated. The residue was extracted with ethanol (50 ml), filtrated, and evaporated to give the title compound in 25% yield.

b: 1-Methyl-3-(5-methyl-1,2,4-oxadiazol-3-yl)-1,2,5,6-tetrahydropyridinium oxalate A solution of 1-methyl-1,2,5,6-tetrahydropyridin-3-carboxamide oxime (200 mg; 1.29 mmol) in acetic anhydride (5 ml) was heated at 80° C. for 24 hours. After evaporation in vacuo the residue was dissolved in 4N NaOH (5 ml) and extracted with ether (3×25 ml). The ether phases were dried (MgSO4), filtered, and evaporated in vacuo. The residue was dissolved in ethanol (99.9%)(5 ml) and added to a solution of oxalic acid (100 mg; 1.1 mmol) in ethanol (99.9%)(5 ml). Addition of ether gave the title compound in a yield of 52%. M.P. 173°–174° C.

EXAMPLE 14

1-Methyl-3-(5-ethyl-1,2,4-oxadiazol-3-yl)-1,2,5,6-tetrahydropyridinium oxalate

The compound was synthesized as described above in Example 13b using propionic anhydride instead of acetic anhydride. Crystallization gave the title compound in 38% yield. M.P. 181°–182° C.

EXAMPLE 15

1-Methyl-3-(5-propyl-1,2,4-oxadiazol-3-yl)-1,2,5,6-tetrahydropyridinium oxalate

The compound was synthesized as described in Example 13b using butyric anhydride instead of acetic anhydride. Crystallization gave the title compound in 65% yield. M.p. 170°–171° C.

EXAMPLE 16 a: 1-Methyl-4-carbamoyl-1,2,5,6-tetrahydropyridinium chloride

To a solution of ammonia in water (25%) (50 ml) was added 1-methyl-4-ethoxycarbonyl-1,2,5,6-tetrahydropyridinium chloride (Lambrecht & Mutschler, Arzneimittel Forsch. (Drug Res.) 23, 1427 (1973)) (4.5 g; 21.9 mmol) and the mixture was stirred at room temperature for 20 hours. After evaporation in vacuo, the residue was recrystallized from methanol and ether. M.P. 191°–192° C.

b: 1-Methyl-4-cyano-1,2,5,6-tetrahydropyridine

A solution of 1-methyl-4-carbamoyl-1,2,5,6-tetrahydropyridinium chloride (3.6 g;20.4 mmol) in sodium hydroxide (4N)(30 ml) was extracted with methylene chloride (3×50 ml). The combined extracts were dried, filtered, and evaporated to 50 ml. To the extract a solution of triphenylphosphine (15.7 g; 60 mmol), bromine (3.3 ml; 65 mmol) and triethylamine (11 ml) in methylenechlorid (150 ml) was added. The reaction was stirred at room temperature for 20 hours and evaporated in vacuo. The residue was dissolved in water (50 ml) and washed with methylene chloride (3×75 ml). To the water-phase sodium hydroxide (4N) (30 ml) was added and the mixture was extracted with methylene chloride. The combined extracts were dried, filtered, and evaporated in vacuo to give the title compound.

c: 1-Methyl-1,2,5,6-tetrahydropyridin-4-carboxamide oxime

The compound was synthesized as described in Example 13a using 1-methyl-4-cyano-1,2,5,6-tetrahydropyridine instead of 1-methyl-3-cyano-1,2,5,6-tetrahydropyridine.

d: 1-Methyl-4-(5-methyl-1,2,4-oxadiazol-3-yl)-1,2,5,6-tetrahydropyridinium oxalate The compound was synthesized as described in Example 13b using 1-methyl-1,2,5,6-tetrahydropyridin-4-carboxamide oxime instead of 1-methyl-1,2,5,6-tetrahydropyridin-3-carboxamide oxime. Crystallization gave the title compound in 13% yield. M-P. 204°–205° C.

EXAMPLE 17

1-Methyl-3-(3-isopropyl-1,2,4-oxadiazol-5-yl)-1,2,5,6-tetrahydropyridinium oxalate 816 mg(8.0 mmol) of isopropylcarboxamide oxime was added to a solution of sodium ethoxide (7.8 mmol) in 20 ml of distilled ethanol and 5 g molecular sieves. The mixture was stirred at room temperature for 10 min whereafter 1.0 g(4.23 mmol) of arecoline,HBr was added. The mixture was heated at 80° C. for 12 hours, filtered, and evaporated in vacuo. 10 ml of water was added to the residue and the mixture was extracted with ether (3×50 ml). The combined extracts were dried with MgSO4 and evaporated in vacuo. The residue was dissolved in 5 ml of 99.9% ethanol and a solution of 380 mg(4.23 mmol) of oxalic acid in 10 ml of 99.9% ethanol was added. Crystallization from ether gave the title compound in 37% yield. M.P. 133°–134° C.

EXAMPLE 18

1-Methyl-3-(3-butyl-1,2,4-oxadiazol-5-yl)-1,2,5,6-tetrahydropyridinium oxalate

The compound was synthesized as described above in Example 17 using pentanamide oxime instead of isopropylcarboxamide oxime. M.P. 121°–123° C.

EXAMPLE 19

3-(3-Ethyl-1,2,4-oxadiazol-5-yl)-1,2,5,6-tetrahydropyridinium oxalate

The compound was synthesized as described in Example 17 using norarecoline, HCl and propionamide oxime instead of arecoline, HBr and isopropylcarboxamide oxime, respectively. M.P. 161°–163° C.

The following compounds were synthesized in exactly the same way using butanamide oxime, pentanamide oxime, cyclopropylcarboxamide oxime, and methoxymethylcarboxamide oxime, respectively.

3-(3-Propyl-1,2,4-oxadiazol-5-yl)-1,2,5,6-tetrahydropyridinium oxalate. M.P. 162°–163° C.

3-(3-Butyl-1,2,4-oxadiazol-5-yl)-1,2,5,6-tetrahydropyridinium oxalate. M.P. 207°–208° C.

3-(3-Cyclopropyl-1,2,4-oxadiazol-5-yl)-1,2,5,6-tetrahydropyridinium oxalate. M.P. 169°–171° C.

3-(3-Methoxymethyl-1,2,4-oxadiazol-5-yl)-1,2,5,6-tetrahydropyridinium oxalate. M.P. 188°–190° C.

EXAMPLE 20 a.

1-Ethyl-3-methoxycarbonyl-1,2,5,6-tetrahydropyridinium chloride 0.509 ml (6.2 mmol) of ethyliodide was added to a mixture of 1.0 g(5.6 mmol) norarecoline and 2.1 g of potassium carbonate in 20 ml of acetone. The reaction mixture was refluxed for 16 hours, filtered, and evaporated in vacuo. The residue was dissolved in 10 ml aqueous 4N sodium hydroxide and was then extracted with ether (3×50 ml). The combined ether phases were dried with (MgSO$_4$), filtered, and evaporated in vacuo. The residue was dissolved in methanol and 10 ml of 2.3N hydrogen chloride in ether was added. Crystallization with ether gave the title compound.

b.

1-Ethyl-3-(3-ethyl-1,2,4-oxadiazol-5-yl)-1,2,5,6-tetrahydropyridinium oxalate

The title compound was synthesized as described in Example 17 using 1-ethyl-3-methoxycarbonyl-1,2,5,6-tetrahydropyridinium chloride and propionamide oxime instead of arecoline, HBr and isopropylcarboxamide oxime, respectively. M.P. 150°–151° C.

EXAMPLE 21

1-Ethyl-3-(3-butyl-1,2,4-oxadiazol-5-yl)-1,2,5,6-tetrahydropyridinium oxalate

The compound was synthesized as described above in Example 20b using pentanamide oxime instead of propionamide oxime. M.P. 102°–104° C.

EXAMPLE 22 a.

1-Propyl-3-methoxycarbonyl-1,2,5,6-tetrahydropyridinium chloride

The compound was synthesized as described in Example 20a using propylbromide instead of ethyliodide. M.P. 173°–174° C.

b.

1-Propyl-3-(3-methyl-1,2,4-oxadiazol-5-yl)-1,2,5,6-tetrahydropyridinium oxalate

The compound was synthesized as described in Example 17 using 1-propyl-3-methoxycarbonyl-1,2,5,6-tetrahydropyridinium chloride and acetamide oxime instead of arecoline, HBr and isopropylcarboxamide oxime, respectively. M.P. 64°–66° C.

EXAMPLE 23

1-Propyl-3-(3-ethyl-1,2,4-oxadiazol-5-yl)-1,2,5,6-tetrahydropyridinium oxalate

The compound was synthesized as described above in Example 22 using propionamide oxime instead of acetamide oxime. M.P. 71°–78° C.

EXAMPLE 24 a.

(RS)-3-Methoxycarbonyl-5-methyl-1,2,5,6-tetrahydropyridinium oxalate

A solution of (RS)-3-carboxy-5-methyl-1,2,5,6-tetrahydropyridinium bromide (Krogsgaard-Larsen et al., Acta chem. Scand. B32, 327–334 (1978)) in saturated methanolic hydrochloric acid was stirred for 17 h at RT and evaporated in vacuo. The residue was dissolved in aqueous sodium hydroxide (4N) and extracted with ether. The combined organic phases were dried (MgSO$_4$), filtered, and evaporated in vacuo. The residue was dissolved in ethanol and a solution of oxalic acid in ethanol was added. Crystallization from ether gave the title compound. M.P. 184°–185° C.

b.

(RS)-5-Methyl-3-(3-ethyl-1,2,4-oxadiazol-5-yl)-1,2,5,6-tetrahydropyridinium oxalate The compound was synthesized as described in Example 17 using (RS)-3-methoxycarbonyl-5-methyl-1,2,5,6-tetrahydropyridinium oxalate and propionamide oxime instead of arecoline, HBr and isopropylcarboxamide oxime, respectively. M.P. 188°–189° C.

EXAMPLE 25

(RS)-5-Methyl-3-(3-butyl-1,2,4-oxadiazol-5-yl)-1,2,5,6-tetrahydropyridinium oxalate The compound was synthesized as described in Example 24b using pentanamide oxime instead of propionamide oxime. M.P. 189°–191° C.

EXAMPLE 26

(RS)-1,6-Dimethyl-3-(3-methyl-1,2,4-oxadiazol-5-yl)-1,2,5,6-tetrahydropyridinium oxalate The compound was synthesized as described in Example 17 using 1,6-dimethyl-3-ethoxycarbonyl-1,2,5,6-tetrahydropyridinium oxalate (Bishop, Z. Naturforsch. 25b, 1249–1251 (1970)) and acetamide oxime instead of arecoline, HBr and isopropylcarboxamide oxime, respectively. M.P. 115°–117° C.

The following compounds were synthesized in exactly the same way using propionamide oxime and pentanamide oxime, respectively.

(RS)-1,6-Dimethyl-3-(3-ethyl-1,2,4-oxadiazol-5-yl)-1,2,5,6-tetrahydropyridinium oxalate. M.P. 148°–149° C.

(RS)-1,6-Dimethyl-3-(3-butyl-1,2,4-oxadiazol-5-yl)-1,2,5,6-tetrahydropyridinium oxalate. M.P. 141°–142° C.

EXAMPLE 27

1-Methyl-3-(5-cyclopropyl-1,2,4-oxadiazol-3-yl)-1,2,5,6-tetrahydropyridinium oxalate 0.182 ml (2.0 mmol) of cyclopropylcarboxylic acid chloride was added to a solution of 200 mg (1.29 mmol) 1-methyl-1,2,5,6-tetrahydropyridin-3-carboxamide oxime in 8 ml DMF. The mixture was stirred at 55° C. for 4 hours and evaporated in vacuo. The residue was refluxed with acetic acid for 16 hours. After evaporation in vacuo the residue was dissolved in 5 ml 4N aqueous sodium hydroxide and was extracted with ether. The combined ether phases were dried with $MgSO_4$ and evaporated in vacuo. The residue contained both the title compound and 1-methyl-3-cyano-1,2,5,6-tetrahydropyridine. After chromatographic separations, the title compound crystallized with oxalic acid from ethanol and ether. M.P. 172°–173° C.

EXAMPLE 28

1-Methyl-4-(5-ethyl-1,2,4-oxadiazol-3-yl)-1,2,5,6-tetrahydropyridinium oxalate

A solution of 1-methyl-1,2,5,6-tetrahydropyridin-4-carboxamide oxime (200 mg; 1.0 mmol) in propionic anhydride (5 ml; 39 mmol) was stirred at 80° C. for 20 hours. After evaporation in vacuo, the residue was dissolved in aqueous sodium hydroxide (4N) (5 ml) and extracted with ether (4×25 ml). The combined ether phases were dried ($MgSO_4$), filtered, and evaporated in vacuo. To a solution of the residue in ethanol (5 ml) a solution of oxalic acid (90 mg; 1.0 mmol) in ethanol (5 ml) was added. Crystallization with ether gave the title compound. M.P. 190°–191° C.

EXAMPLE 29

1-Methyl-4-(5-cyclopropyl-1,2,4-oxadiazol-3-yl)-1,2,5,6-tetrahydropyridinium oxalate The compound was synthesized as decribed in Example 27 using 1-methyl-1,2,5,6-tetrahydropyridin-4-carboxamide oxime instead of 1-methyl-1,2,5,6-tetrahydropyridin-3-carboxamide oxime. M.P. 173°–174° C.

EXAMPLE 30

(RS)-3-Methyl-5-(3-ethyl-1,2,4-oxadiazol-5-yl)-1,2,5,6-tetrahydropyridinium oxalate The compound was synthesized as described in Example 17 using (RS,RS,RS)-4-hydroxy-5-methyl-3-methoxycarbonylpiperidinium chloride (Krogsgaard-Larsen et al., Acta Chem. Scand. B32, 327–334 (1978)) and propionamide oxime instead of arecoline, HBr and isopropylcarboxamide oxime, respectively. M.P. 186°–187° C.

EXAMPLE 31

1-methyl-3-(3-(2-thienyl)-1,2,4-oxadiazol-5-yl)-1,2,5,6-tetrahydropyridinium oxalate The compound was synthesized as described above in Example 1 using 2-thiophen carboxamide oxime instead of methoxymethyl carboxamide oxime. Crystallization gave the title compound in 46% yield. M.P. 149°–150° C.

EXAMPLE 32

1-methyl-3-(3-octyl-1,2,4-oxadiazol-5-yl)-1,2,5,6-tetrahydropyridinium oxalate

The compound was synthesized as described above in Example 1 using nonanamide oxime instead of methoxymethyl carboxamide oxime. Crystallization gave the title compound in 19% yield. M.P. 122°–123° C.

EXAMPLE 33

1-methyl-3-(3-pentyl-1,2,4-oxadiazol-5-yl)-1,2,5,6-tetrahydropyridinum oxalate

The compound was synthesized as described above in Example 1 using hexanamide oxime instead of methoxymethyl carboxamide oxime. Crystallization gave the title compound in 40% yield. M.P. 149°–150° C.

EXAMPLE 34

1-methyl-3-(3-heptyl-1,2,4-oxadiazol-5-yl)-1,2,5,6-tetrahydropyridinium oxalate

The compound was synthesized as described above in Example 1 using octanamide oxime instead of methoxymethyl carboxamide oxime. Crystallization gave the title compound in 33% yield. M.P. 94°–95° C.

EXAMPLE 35

3-(3-methyl-1,2,4-oxadiazol-5-yl)-1,2,5,6-tetrahydropyridinium oxalate

The compound was synthesized as described above in Example 17 using norarecoline, HCl and acetamide oxime instead of arecoline, HBr and isopropyl carboxamide oxime, respectively. M.P. 172°–173° C.

EXAMPLE 36

3-(3-isopropyl-1,2,4-oxadiazol-5-yl)-1,2,5,6-tetrahydropyridinium oxalate

The compound was synthesized as described above in Example 17 using norarecoline, HCl instead of arecoline, HBr. M.P. 199°–200° C.

EXAMPLE 37

3-(3-phenyl-1,2,4-oxadiazol-5-yl)-1,2,5,6-tetrahydropyridinium oxalate

The compound was synthesized as described above in Example 17 using norarecoline, HCl and benzamide oxime instead of arecoline, HBr and isopropyl carboxamide oxime, respectively. M.P. 208°–209° C.

EXAMPLE 38

3-(3-(2-thienyl)-1,2,4-oxadiazol-5-yl)-1,2,5,6-tetrahydropyridinium oxalate

The compound was synthesized as described above in Example 17 using norarecoline, HCl and 2-thiophene carboxamide oxime instead of arecoline, HBr and isopropyl carboxamide oxime, respectively. M.P. 199°–200° C.

EXAMPLE 39

1-methyl-4-(3-ethyl-1,2,4-oxadiazol-5-yl)-1,2,5,6-tetrahydropyridinium oxalate

Propionamide oxime (440 mg; 5,0 mmol), dicyclohexylcarbodiimide (1030 mg; 5.0 mmol) and 4-carboxy-1-methyl-1,2,5,6-tetrahydropyridinium chloride (886 mg; 5,0 mmol) were mixed in distilled DMF. The mixture was stirred at 60° C. for 1 1/2 hours and evaporated in vacuo. To the residue was added water (50 ml) and the mixture was extracted with toluene (3×75 ml). pH was adjusted to 10 by means of 4N NaOH and extracted with toluene (3×100 ml). The combined extracts were dried (Na2SO4) and evaporated in vacuo. Upon dissolving the residue in ethanol (99.9%) (5 ml) a solution of oxalic acid (360 mg; 4,0 mmol) in ethanol (99,9%) (5 ml) was added. Crystallization gave the title compound in 15% yield. M.P. 170°–171° C.

EXAMPLE 40

1-methyl-4-(3-phenyl-1,2,4-oxadiazol-5-yl)-1,2,5,6-tetrahydropyridinium oxalate

The compound was synthesized as described above in Example 39 using benzamide oxime instead of propionamide oxime. M.P. 172°–173° C.

From the foregoing Table 1 it is apparent that the compounds of the present invention exhibit a high degree of affinity for the muscarinic cholinergic receptors and are muscarinic cholignergic agonists.

In conclusion, from the foregoing Table 1 it is apparent that the present invention provides novel compounds which are useful in stimulating the cognitive functions of the forebrain and hippocampus, and which are therefore useful in the treatment of Alzheimer's disease, which compounds are oxadiazolyl-piperidine compounds and addition salts thereof, having the said highly advantageous and unpredictable properties. Further, a new synthesis is provided by the present invention.

It is to be understood that the invention is not to be limited to the exact details of operation, or to the exact compounds, compositions, methods, procedures, or embodiments shown and described, as obvious modifications and equivalents will be apparent to one skilled in the art and the invention is therefore to be limited only by the full scope of the appended claims.

We claim:

1. Piperidine compound selected from (A) those having the formula I

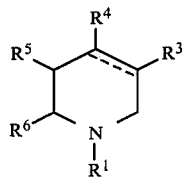

wherein
at least one of $R^3$, $R^4$, and $R^5$ is

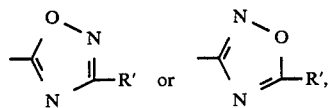

and the others independently are H or $C_{1-6}$-alkyl, and
wherein R' is methoxymethyl; and
$R^1$ and $R^6$ independently are H or $C_{1-6}$-alkyl,

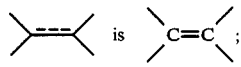

and (B) a salt thereof with a pharmaceutically-acceptable acid.

2. A compound of claim 1 which is 1-methyl-3-(3-methoxymethyl-1,2,4-oxadiazol-5-yl)-1,2,5,6-tetrahydropyridine.

3. A compound of claim 1 which is 3-(3-methoxymethyl-1,2,4-oxadiazol-5-yl)-1,2,5,6-tetrahydropyridine.

4. A pharmaceutical composition suitable for use in stimulating the cognitive functions of the forebrain and hippocampus of mammals, including humans, and therefore in treating Alzheimer's disease, comprising an amount of a compound of claim 1, 2, or 3 which is effective for the stimulation of the forebrain and hippocampus of mammals or treating Alzheimer's disease together with a pharmaceutically-acceptable carrier or diluent.

5. A pharmaceutical composition according to claim 4 in the form of an oral dosage unit containing 1–100 mg of the compound.

6. A method of stimulating the cognitive functions of the forebrain and hippocampus and of therefore of treating Alzheimer's disease in a subject in need of such stimulation and/or treatment, comprising the step of administering to said subject an amount of a compound of claim 1, 2, or 3, which is effective for such purpose.

7. A method of claim 6, wherein said compound is administered in the form of a pharmaceutical composition together with a pharmaceutically-acceptable carrier or diluent.

* * * * *

UNITED STATES PATENT AND TRADEMARK OFFICE
CERTIFICATE OF CORRECTION

PATENT NO. : 4,933,353

DATED : June 12, 1990

INVENTOR(S) : Leif H. Jensen, Per Sauerberg, Frank Wätjen, Jens W. Kindtler

It is certified that error appears in the above-identified patent and that said Letters Patent is hereby corrected as shown below:

Title Page, [73] Assignee:"Sydmarken, Fed. Rep. of Germany" should read -- Søborg, Denmark --.

Title Page, OTHER PUBLICATIONS, "Iverson," should read -- Iversen, --

Column 2, line 11; "acids" should read -- acid --.

Column 4, line 18; "11 µg/ml)." should read -- 110µg/ml). -- .

Column 5/6, Table 1, Continued, 6th column heading;

" 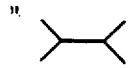 "       should read        --

Column 7, line 48; "disolving" should read -- dissolving --.

Column 13, line 53;"decribed" should read -- described --.

Column 14, line 21,22; "tetrahydropyridinum" should read -- tetrahydropyridinium --.

Column 15, line 19;"(Na2SO$_4$)" should read --(Na$_2$SO$_4$) --.

Column 16, line 50; delete "of", first occurrence.

UNITED STATES PATENT AND TRADEMARK OFFICE
CERTIFICATE OF CORRECTION

PATENT NO. : 4,933,353

DATED : June 12, 1990

INVENTOR(S) : Leif H. Jensen, et al

It is certified that error appears in the above-identified patent and that said Letters Patent is hereby corrected as shown below:

Column 15, line 54, "art and" should read --art, and --.

Signed and Sealed this

Eighth Day of October, 1991

Attest:

HARRY F. MANBECK, JR.

*Attesting Officer*          *Commissioner of Patents and Trademarks*